US009372267B2

(12) United States Patent
Li et al.

(10) Patent No.: US 9,372,267 B2
(45) Date of Patent: Jun. 21, 2016

(54) APPARATUS AND METHODS FOR PHOTOSENSOR QUADRANT SHARING

(71) Applicant: Board of Regents, The University of Texas System, Austin, TX (US)

(72) Inventors: Hongdi Li, Pearland, TX (US); Wai-Hoi Wong, Houston, TX (US); Yuxuan Zhang, Pearland, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 103 days.

(21) Appl. No.: 14/085,246

(22) Filed: Nov. 20, 2013

(65) Prior Publication Data

US 2014/0138548 A1    May 22, 2014

Related U.S. Application Data

(60) Provisional application No. 61/728,327, filed on Nov. 20, 2012.

(51) Int. Cl.
*G01T 1/20* (2006.01)
*G01T 1/164* (2006.01)
*A61B 6/03* (2006.01)

(52) U.S. Cl.
CPC .............. *G01T 1/1644* (2013.01); *A61B 6/037* (2013.01)

(58) Field of Classification Search
CPC ....... G01T 1/1644; G01T 1/20; G01T 1/2006; G01T 1/208; A61B 6/037; A61B 5/0059; A61B 6/0478; A61B 6/4225; A61B 6/501
USPC ....................................................... 250/366
See application file for complete search history.

(56) References Cited

U.S. PATENT DOCUMENTS

| 5,319,204 A | 6/1994 | Wong |
| 5,453,623 A | 9/1995 | Wong et al. |
| 5,825,031 A * | 10/1998 | Wong et al. .............. 250/363.03 |
| 6,956,214 B2 * | 10/2005 | Wong et al. ................... 250/368 |
| 7,238,943 B2 * | 7/2007 | Wong et al. ................... 250/367 |
| 2003/0226972 A1* | 12/2003 | Wong et al. ................... 250/368 |
| 2004/0021082 A1* | 2/2004 | Wong et al. ................... 250/367 |

OTHER PUBLICATIONS

Ramirez, et al., "A Lower-Cost High-Resolution LYSO Detector Development for Positron Emission Mammography (PEM)," *IEEE Transactions on Nuclear Science*, 56(5):2621-2627, 2009.
Ramirez, et al., "High-Resolution L(Y)SO Detectors Using PMT-Quadrant-Sharing for Human & Animal PET Cameras," *IEEE Transactions on Nuclear Science*, 55(3):862-869, 2008.
Surti, et al., "Design Evaluation of A-PET: A High Sensitivity Animal PET Camera," *IEEE Transactions on Nuclear Science*, 50(5):1357-1363, 2003.
Surti, et al., "Performance of Philips Gemini TF PET/CT Scanner with Special Consideration for Its Time-of-Flight Imaging Capabilities," *J. Nucl. Med.*, 48(3):471-480, 2007.

(Continued)

*Primary Examiner* — David J Makiya
*Assistant Examiner* — Taeho Jo
(74) *Attorney, Agent, or Firm* — Parker Highlander PLLC

(57) ABSTRACT

Apparatus and methods comprising a positron emission tomography detector having a first rectangular cross-section crystal block positioned between a first pentagonal cross-section crystal block and a second pentagonal cross-section crystal block.

13 Claims, 11 Drawing Sheets

(56) References Cited

OTHER PUBLICATIONS

Wong, et al., "An elongated position sensitive block detector design using the PMT quadrant-sharing configuration and asymmetric light partition," *IEEE Transactions on Nuclear Science*, 46(3):542-545, 1999.

Wong, et al., "Design of an Inexpensive High-Sensitivity Rodent-Research PET Camera (RRPET)," 2003 *Nuclear Science, IEEE Transactions*, 50(3):2058-2062, 2003.

Wong, et al., "Engineering and Performance (NEMA and Animal) of a Lower-Cost Higher-Resolution Animal PET/CT Scanner Using Photomultiplier-Quadrant-Sharing Detectors," *J Nucl. Med.*, 53(11):1786-1793, 2012.

Wong, et al., "Performance Evaluation of the Low Cost and High Sensitivity Rodent-Research PET (RRPET) Camera Using Monte Carlo Simulations," 2005 IEEE Nuclear Science Symposium and Medical Imaging Conference, Oct. 23-29, 2005.

Xie, et al., "A Pentagon Photomultiplier-Quadrant-Sharing BGO Detector for a Rodent Research PET (RRPET)," *IEEE Transactions on Nuclear Science*, 52:210-216, 2005.

Zhang, et al., "The System Design, Engineering Architecture and Preliminary Results of a Lower-cost High-Sensitivity High-Resolution Positron Emission Mammography Camera," *IEEE Transactions on Nuclear Science*, 57(1):104-110, 2010.

\* cited by examiner

APPARATUS AND METHODS FOR PHOTOSENSOR QUADRANT SHARING

The present application claims benefit of priority to U.S. Provisional Application Ser. No. 61/728,327, filed Nov. 20, 2012, the entire contents of which are hereby incorporated by reference.

This invention was made with government support under contracts 5RO100EB4840 and 2RO1EB001038 awarded by NIH/NIBIB. The government has certain rights in this invention.

BACKGROUND INFORMATION

Positron emission tomography (PET) can detect tumor in vivo based on the living chemistry of cancer tissues. In recent years, PET has well demonstrated its broad clinical utilities in cancer diagnosis and is recognized as an important tool to study cancer functions in vivo, because of its unique ability to elicit molecular functions. The in vivo molecular imaging ability of PET has triggered considerable cancer-research interest and radiotracer development to study cancer related molecular processes such as angiogenesis, apoptosis, cell proliferation, hypoxia, gene expression and blood flow.

Despite this success, the cancer-application potential of PET in whole body is still largely untapped today because of high scanner cost, and low image resolution. As of 2009, clinical PET cameras have imaging resolution of 4.0-6.3 mm, but because of low sensitivity, the practical clinical resolution is worse (7-10 mm), which can miss smaller (early) primary lesions and metastases. In the last decade, researchers have focused on the development of low-cost ultrahigh resolution PET technologies and PET cameras.

PET camera detectors are made up of tens of thousands of scintillation crystals and thousands of photosensors. The most commonly used photosensors in clinical PET cameras are photomultiplier tubes (PMT). Although other solid-state or semiconductor photosensors are also being investigated, such sensors are currently more expensive than PMT.

Photomultiplier tubes (PMT) are used to detect scintillation signals from scintillation crystals and convert the signal into electronic signals. In certain existing embodiments, an array or block of scintillation crystal elements (pixels) are coupled to the four or more PMT's. These four PMT's detect the light from a scintillating crystal element and decode the position of the scintillating crystal within the block. Each crystal element (pixel) distributes a unique ratio of light to each of the four PMT. The unique ratio of light distribution from each pixel to the four or more PMT is the signature of each pixel for decoding that pixel. One of the typical designs is shown in FIGS. 1 and 2.

PMT cost is a major component cost in a PET detector system. For example, in a typical clinical PET, about 1,200 PMT are used (e.g. DST PET-CT available from GE® Corporation) and each PMT channel costs $250-300 (with high voltage circuit and amplifiers). Accordingly, reducing the number of PMT used can lower the production cost of PET scanners, and making the crystal elements smaller can improve the imaging resolution of PET cameras. To reduce the number of PMT used, and to improve the image resolution of PET camera, a detector design utilizing "Photomultiplier Quadrant Sharing" (PQS) was developed as shown in FIGS. 3 and 4 (and as described in U.S. Pat. Nos. 5,319,204; 5,453,623; 6,956,214 and 7,238,943). Current exemplary embodiments of the PQS design are not confined to using photomultiplier tubes, but can also use solid state photosensors. Accordingly, the term "PQS" has been updated to mean "Photosensor-Quadrant-Sharing" in this disclosure.

In the PQS design, each quadrant of a PMT is placed adjacent to one quadrant of each detector block/array. The PQS design reduces the number of PMT used by seventy-five percent because each PMT measures the light output of four arrays instead of one array, thus replacing four PMT with one PMT. By the same token, if the same size PMT and the same number of PMT are used, the detector pixel can be reduced by seventy-five percent, quadrupling the number of pixels in the camera. Since the two dimensional data acquired is used to generate a three-dimensional tomography image, the camera imaging volume or voxel size is decreased by eight times using the PQS design. Accordingly, the PQS design may be used to detect cancer lesions that are one-eighth the size of those detectable by non-PQS designs, without increasing the production costs of the current clinical systems.

Generally, there are two methods to distribute light from each crystal pixel of a block/array to the four PMT for decoding the position of a firing crystal. One method is to have the crystal block or array coupled to a light guide with different saw-cut depths (see FIGS. 1 and 3). This light guide is then coupled to four PMT, either in the conventional way (see FIG. 1) or in the PQS configuration (see FIG. 3). A second method is to distribute light from the firing crystal through adjacent crystal pixels in the block to four PMT (see e.g., FIGS. 2 and 4). There are two approaches to implement this second method. For example, embodiments provided by GE® Corporation uses crystals with different surface finishes (on the 4 cylindrical sides) to control the amount of light crossover from one crystal to the next. However, since there are only a limited effective surface finishes that can be used, the number of crystals that can be decoded by the four PMT is more limited. The smaller number of crystal pixels in a block/array leads to lower imaging resolution. The second approach, developed by the inventors of the exemplary embodiments disclosed herein, uses partial reflectors (white paint or mirror film) applied to each surface of each pixel as shown in FIG. 5.

FIG. 1 displays a conventional PET detector array using external light guides to distribute light from scintillation detector pixels to four PMT, while FIG. 2 displays a conventional PET array using internal light distribution to distribute light to four PMT. FIG. 3 illustrates a PQS array using an external light guide and the same size PMT as FIGS. 1 and 2. The FIG. 3 configuration can provide much smaller detector pixels (higher imaging resolution), or utilize a PMT that is four times larger to provide the same size detector pixel (to reduce the number of PMT used). FIG. 4 illustrates a PQS array using internal light distribution to increase resolution or reduce PMT cost.

Partial reflectors can be used for controlling a desirable amount of light bleeding to a neighboring crystal pixel. FIG. 5 illustrates the partial reflectors (e.g., paint) applied to the detector pixels in a block. Since the partial reflector can have infinite sizes and shapes, many more crystals pixels can be decoded by four PMT, leading to higher resolution. Inventors of exemplary embodiments disclose herein have also invented and patented a manufacturing method (Slab-Sandwich-Slice or SSS method) to efficiently and accurately produce position-decoding blocks. Again, this partial reflector block-detector design can be coupled to four PMT conventionally (FIG. 2) or in PQS configuration (FIG. 4).

PQS can therefore either be used to lower the cost of nuclear camera production cost or improve the imaging resolution of cameras, or both. With continuous design improvement on the internal structure of PQS detectors, the inventors have achieved much more than four times higher detector pixel resolution. Exemplary embodiments of the PQS detectors developed by the inventors can decode 256 detectors per photosensor, while the current GE® Corporation PET camera decodes 14 detectors per photosensor. The current Siemens® PET camera decodes 42 detectors per photosensor and the current Philips® PET camera decodes an average of 67 detectors per photosensor. Therefore, the current PQS detector design has 5.4-18 times more detector pixels per photosensor than current clinical PET, which translates to 12.5-76 times smaller voxels size in the tomographic image of a PQS camera, which is significant in detecting much smaller cancer lesion volume or much earlier cancer, thereby enabling better prognosis and cancer management.

The PQS detector design is typically implemented in the form of rectangular detector panels as shown in FIG. 6. However, in PET cameras, the PET detectors generally form a detection ring circumscribing the subject as shown in FIG. 7.

For SPECT cameras, although a detector ring is not needed, a large curve detector panel would allow the detector to be placed closer to the body contours (such as cardiac studies) to achieve higher SPECT resolution and sensitivity. To form a ring or curve detection system, multiple PQS detector panels can be placed next to each other to form a polygonal ring or curve, but PQS generally requires a detector-free zone (no scintillation crystal) that is the size of a half of a photosensor at each of the 4-edges of a rectangular panel as shown in FIG. 6. Hence, placing PQS panels adjacent to each other to form a detector ring or curve would cause a detector gap of one photosensor size between two detector panels. The detection gaps are not desirable for several reasons: (a) lower detection sensitivity, (b) inadequate data sampling unless the detection system rotates, which increases mechanical complexity, reliability, positioning errors and production cost. For the new "time-of-flight" PET applications, the detection gap without rotating the detection system is especially problematic in the image reconstruction process.

As shown in FIGS. 6 and 7, the scintillation blocks form detector arrays that are coupled to the PMT to form large detector panels. The panels can be placed proximal to each other to form a ring as shown in FIG. 7. As shown in FIGS. 6 and 7, the gaps between two panels on the ring are equal to or larger than one PMT size (half a PMT on each adjacent panel) because the blocks do not entirely cover the circular PMTs at the ends of the array.

For a large camera system with 12 PQS detector panels similar to that shown in FIG. 7, hundreds of photosensors detection channels (photosensors and supporting electronics) can be saved to further lower the production cost of a camera using the PQS detector design.

A continuous PET detector ring or partial ring using the PQS design can be implemented that eliminates the gaps between the panels shown in FIG. 7. As illustrated in FIG. 8, for this configuration four surfaces of each detector block must be precisely tapered to form a symmetric pentagon. The pentagonal blocks can then be butted against each other to form a ring or partial ring as shown in FIG. 7. This configuration is compatible the PQS design whereby each quadrant of each photosensor is placed adjacent to a quadrant of a scintillation crystal array.

While the configuration shown in FIG. 7 addresses some of the shortcomings of prior systems, it also results in high manufacturing costs for large scale systems.

One straightforward way to implement a PQS technology is to pack many crystal arrays/blocks into a large panelized detector module and circumscribe the imaged object by a relatively small number (e.g., four or six) such detector panels. However, there is degradation in image resolution even for the region near the center of the field-of-view and sensitivity loss caused by the gaps between two detector panels. The earlier generations of the PennPET (University of Pennsylvania) with an hexagonal detector ring demonstrated such effects, which led to the "circularization" of the later PennPET (Philips NaI PET) using curved NaI(Tl) crystals.

In one embodiment, the gap between two panels of a HOTPET camera in brain mode is 14.8 mm, and 12 such gaps cause at least a ten percent loss of the detection sensitivity. While an accurate rotation gantry can be used to rotate the apparatus and fill the gaps of missing LOR in the sinograms, such an implementation also increases the production cost.

For generally smaller detector ring designs, each detector array/block can be placed "archually" on the detector circle. To "circularize" the PQS design, which requires two adjacent arrays to share the same PMT, each detector array/block has to be ground (by a small amount) to a slightly pentagonal shape as shown in FIG. 8. On the circumferential dimension, the last two rows of crystals in each block/array also needed to be ground down to a slight taper.

In exemplary embodiments of the design shown in FIG. 8, each detector block can be manufactured from a rectangular cross-section block first by placing the block into a form (or jig) to be ground down on four surfaces to the desired shape. With tapered end-crystals in each block, all the adjacent blocks are glued together to form a solid cylindrical ring, thus providing almost one hundred percent packing fraction with the highest possible detection sensitivity.

Existing systems, including Philips® Medical System, include a close-to-gapless PET detector ring using a modular design with each detector module consisting of an array of optically isolated scintillation crystals. In certain embodiments, this crystal array is coupled to a thick (e.g., 25 mm) solid piece of light transparent material to disperse the light. This solid transparent plastic piece is curved or slanting on the output end. In such embodiments, the solid curved light guide can then be coupled to a large array of PMT. In particular embodiments using this configuration, the scintillation light is distributed to all fifteen PMT coupled to the whole detector module (though the position is determined by the nearest seven PMT), which is more than the four PMT in the PQS design. In certain embodiments, the design is essentially a conventional gamma camera Anger-logic positioning design modified from a flat camera head to a curve camera head.

In such embodiments, the light guide (a) absorbs light signal and (b) reduces the light going to the PMT by a wide area light dispersion (larger than the seven PMT used for extracting the scintillating position), thereby reducing the positioning signal strength and positioning accuracy. Furthermore, in traditional gamma camera, it is known that the probability of gamma-event "pileups" (e.g., one, two, or three events hitting the detector head during the processing of a prior event) is higher in such a large detector head with all the PMT receiving light from all the crystal pixels.

SUMMARY

As explained in more detail below, exemplary embodiments of the present disclosure enable the lower cost, higher resolution PQS detector design to be used to make PET detector rings and polygonal SPECT detector panels more economically and with no detection gaps. Such a configuration can provide increasing detection sensitivity, and improving data sampling and reliability without expensive, high-precision camera rotation movement. Exemplary embodiments of the present disclosure can utilize the PQS configuration illustrated in FIGS. 3 and 4.

Embodiments of the current disclosure also reduce the number of photosensors used in the camera from the original panelized PQS design. As explained in further detail below, the original PQS design would waste one half of the photosensors along each edge of each panel. In exemplary embodiments of this disclosure with a gapless continuous ring, such waste is eliminated.

Unlike existing embodiments described in the previous section, in the PQS design the light signal is confined to go to just four PMT, thus having lower pileup of event signals. Accordingly, there are several advantages exemplary embodiments in forming a gapless PQS PET detector ring compared with other existing systems that incorporate a ring that is nearly gapless.

For example, embodiments of the gapless PQS detector ring result in less signal pileup that degrades the image quality. In addition, more light signal is available for position-decoding of the scintillating crystal pixel, thus higher imaging resolution. Embodiments of the gapless PQS detector ring also provide better time-of-flight resolution, since timing resolution is proportional to the amount of signal light used for determining the time of arrival of an event. The gapless PQS design channels all the light to just four PMT, while the existing designs disperse the light from each crystal to a higher number (e.g. fifteen) of PMTs and just use the signal collected by the nearby PMTs for timing measurement and position measurement. Furthermore, the thick light guide utilized in other embodiments absorbs and loses more light compared to gapless PQS designs that do not use an external light guide.

Accordingly, gapless PQS designs can have better timing and position/imaging resolution than the designs using a curved or slanting solid light guide. Furthermore, gapless detector rings using the PQS design with internal light guides will have even better timing and positioning/imaging resolution than those using external light guides.

In one example of the above-described resolution improvement resulting from more efficient light detection, a gapless PQS detector design can decode 200-256 crystals per PMT, while the curved or slanting solid light guide can only decode 67 crystals per PMT on a system level. Other existing embodiments (e.g. Siemens® PET) decodes 42 crystals per PMT while another embodiment (e.g. GE® PET) decodes 14 crystals per PMT.

This data shows the significant advantage of imaging resolution improvement using the PQS design compared to other current clinical human PET system. As an analogy to digital photographic camera, if the GE® system with 14 crystals per PMT is a 1 mega-pixel digital camera, the Siemens® PET would be a 3 mega-pixel camera, the Philips® PET would be a 3.4 mega pixel camera, and embodiments of the present gapless PQS design would be an 18 mega-pixel camera.

Hence, applying the PQS detector design to make a gapless PET detector ring or polygon can lead to much improved imaging resolution and time-of-flight resolution that reduces noise in PET images. However, in order to produce human scale detectors, it is necessary to address several manufacturing obstacles that exist with designs utilizing pentagonal crystal blocks as shown in FIG. 8.

In the design shown in FIG. 8, it is necessary to modify (e.g., grind) all the detector blocks into tapered-pentagons. The individual block grinding may be more acceptable for a PET configured for animal testing, as the number of crystal blocks to be ground is small. But for a human-scale PET system, with a hundred times more detector blocks, such individual block grinding can be prohibitively expensive.

Embodiments of the gapless PET detector disclosed herein provide for lower manufacturing cost while maintaining high resolution.

For the sake of simplicity in illustration, all the detectors blocks/array shown in this disclosure will represent the configurations shown in both FIGS. 3 and 4, without explicitly drawing out the light guide. For example, each detector pixel illustrated herein is intended to depict a detector pixel with partial reflectors on the four cylindrical surfaces, as well as a detector pixel with its light-guide portion attached to the light-output end of the scintillation crystal pixel.

In one embodiment, a gapless PQS detector ring or polygon scaled for a human brain consists of 20 detector panels, with each panel having 48 PQS blocks configured as 4 (in circumferential direction)×12 (in axial direction) arrays. Certain embodiments, in addition to using the normal PQS detector design, also uses elongated asymmetric PQS-blocks design along the two edges of each detector panel to increase the usable axial field of view.

Certain embodiments of the present disclosure may include an apparatus comprising: a plurality of photosensors, and a first array of scintillation crystals coupled to the plurality of photosensors, where the first array of scintillation crystals comprises a first rectangular cross-section crystal block positioned between a first pentagonal cross-section crystal block and a second pentagonal cross-section crystal block.

Specific embodiments may further comprise a second rectangular cross-section crystal block positioned between the first pentagonal cross-section crystal block and the second pentagonal cross-section crystal block. Particular embodiments may further comprise a third rectangular cross-section crystal block positioned between the first and second rectangular cross-section crystal blocks. Certain embodiments may further comprise N number of arrays of scintillation crystals coupled to the plurality of photosensors configured as a continuous polygonal detector-ring.

In specific embodiments, the first pentagonal cross-section crystal block may comprise a first side adjacent to the first rectangular cross-section block, the first side of the first pentagonal cross-section crystal block being perpendicular to a second side and to a third side of the first pentagonal cross-section crystal block. In addition, the second pentagonal cross-section crystal block may comprise a first side adjacent to the second rectangular cross-section block, the first side of the second pentagonal cross-section crystal block being perpendicular to a second side and to a third side of the second pentagonal cross-section crystal block.

In particular embodiments, the first pentagonal cross-section crystal block may comprise a fourth side configured at a first taper angle relative to the first and third sides of the first pentagonal cross-section crystal block; the first pentagonal cross-section crystal block may comprise a fifth side configured at a second taper angle relative to the second side of the first pentagonal cross-section crystal block; and the first taper angle may be equal to the second taper angle. In certain embodiments, the first and second taper angles are equal to (180°/N). In specific embodiments, the apparatus may be configured as a positron emission tomography detector and the photosensors may be photomultiplier tubes.

In particular embodiments, a first photomultiplier tube and a second photomultiplier tube may be adjacent and parallel to each other; the first photomultiplier tube and the second photomultiplier tube may be disposed between a third photomultiplier tube and a fourth photomultiplier tube; the third photomultiplier tube and the fourth photomultiplier tube may not be parallel to each other; and the third photomultiplier tube and the fourth photomultiplier tube may not be parallel to the first and second photomultiplier tubes.

In specific embodiments, the first pentagonal cross-section crystal block may comprises a first side that is parallel to a second side, where the first side extends across the length of the first pentagonal cross-section crystal block; and the second side extends more than half of the length of the first pentagonal cross-section crystal block.

Particular embodiments may include an apparatus comprising a plurality of photomultiplier tubes coupled to a plurality of scintillation crystal arrays configured as a continuous detector-ring, where each scintillation crystal array comprises a plurality of rectangular cross-section crystal blocks and a plurality of asymmetric pentagonal cross-section crystal blocks; and each of the rectangular cross-section crystal blocks are positioned between a pair of asymmetric pentagonal cross-section crystal blocks.

In certain embodiments, each of the rectangular cross-section crystal blocks may be adjacent to an asymmetric pentagonal cross-section crystal block and to a rectangular cross-section crystal block. Specific embodiments may include a pair of rectangular cross-section crystal blocks that are positioned between a pair of asymmetric pentagonal cross-section crystal blocks. Particular embodiments may include three rectangular cross-section crystal blocks that are positioned between a pair of asymmetric pentagonal cross-section crystal blocks.

In certain embodiments the continuous detector-ring may comprise a first and second axial end, the first and second axial end comprising a plurality of scintillation crystal arrays having crystal blocks with a greater axial length than circumferential length. In particular embodiments, the plurality of asymmetric pentagonal cross-section crystal blocks may comprises a first asymmetric pentagonal cross-section crystal block comprising: a first side that is parallel to a second side; the first side extends across the length of the first pentagonal cross-section crystal block; and the second side extends more than half of the length of the first pentagonal cross-section crystal block.

Certain embodiments may also include an apparatus comprising: a plurality of scintillation crystal arrays and photomultiplier tubes configured as a continuous detector-ring having a circumferential direction and an axial direction. In specific embodiments, the plurality of scintillation crystal arrays may be coupled to the plurality of photomultiplier tubes; and the scintillation crystal array may comprise an alternating pattern of rectangular cross-section crystal blocks and pentagonal cross-section crystal blocks in the circumferential direction.

In particular embodiments, the alternating pattern may comprise two adjacent rectangular cross-section crystal blocks positioned between two pentagonal cross-section crystal blocks in the circumferential direction. In certain embodiments, the alternating pattern may comprise three adjacent rectangular cross-section crystal blocks positioned between two pentagonal cross-section crystal blocks in the circumferential direction. In specific embodiments, the alternating pattern may comprise four adjacent rectangular cross-section crystal blocks positioned between two pentagonal cross-section crystal blocks in the circumferential direction. In particular embodiments, the alternating pattern may comprise five adjacent rectangular cross-section crystal blocks positioned between two pentagonal cross-section crystal blocks in the circumferential direction. In certain embodiments, the continuous detector-ring may comprise a first and second axial end, the first and second axial end comprising a plurality of scintillation crystal arrays having crystal blocks with a greater axial length than circumferential length.

Specific embodiments may also include a method comprising: obtaining a plurality of rectangular cross-section scintillation crystal blocks; modifying a first rectangular cross-section scintillation crystal block by tapering two sides of the first rectangular cross-section scintillation crystal block to form a first asymmetric pentagonal cross-section scintillation crystal block; modifying a second rectangular cross-section scintillation crystal block by tapering two sides of the second rectangular cross-section scintillation crystal block to form a second asymmetric pentagonal cross-section scintillation crystal block; and arranging the first and second asymmetric pentagonal cross-section scintillation crystal blocks and a third rectangular cross-section scintillation crystal block so that the third rectangular cross-section scintillation crystal block is located between the first and second asymmetric pentagonal cross-section scintillation crystal blocks. Certain embodiments may further comprise arranging a fourth rectangular cross-section scintillation crystal block between the first and second asymmetric pentagonal cross-section scintillation crystal blocks.

Particular embodiments may further comprise coupling the first asymmetric pentagonal cross-section scintillation crystal block to the third rectangular cross-section scintillation crystal block and coupling the second asymmetric pentagonal cross-section scintillation crystal block to the fourth rectangular cross-section scintillation crystal block. Specific embodiments may further comprise arranging a plurality of rectangular cross-section scintillation crystal blocks between the first and second asymmetric pentagonal cross-section scintillation crystal blocks. Certain embodiments may further comprise coupling the first and second asymmetric pentagonal cross-section scintillation crystal block to the third rectangular cross-section scintillation crystal block. In particular embodiments, tapering two sides of the first and second rectangular cross-section scintillation crystal blocks may comprise grinding the two sides.

In specific embodiments, the first and second asymmetric pentagonal cross-section scintillation crystal blocks each may comprise a first side that is perpendicular to a second side and perpendicular to a third side; and the first side of the first and second asymmetric pentagonal cross-section scintillation crystal blocks may be coupled to the third rectangular cross-section scintillation crystal block.

Particular embodiments may include an array of scintillation crystal blocks, comprising: a first asymmetric pentagonal cross-section scintillation crystal block; a second asymmetric pentagonal cross-section scintillation crystal block; and a rectangular cross-section scintillation crystal block disposed between the first and second asymmetric pentagonal cross-section scintillation crystal blocks. In certain embodiments, the first and second asymmetric pentagonal cross-section scintillation crystal blocks may each comprise a first side that is perpendicular to a second side and perpendicular to a third side. In specific embodiments, the rectangular cross-section scintillation crystal block may be adjacent to the first side of the first and second asymmetric pentagonal cross-section scintillation crystal blocks.

In the following, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF ILLUSTRATIVE EMBODIMENTS

Figure 9:
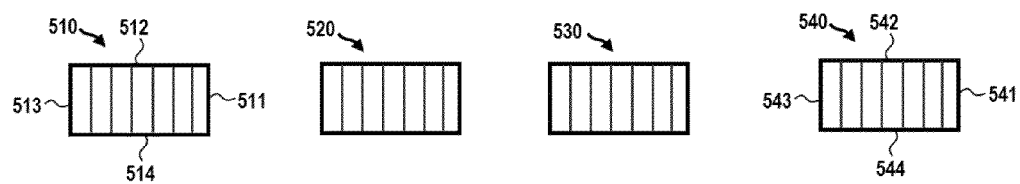
FIGS. 9-11 display a plurality of rectangular cross-section scintillation crystal blocks used to form an array of blocks.
Figure 10A:
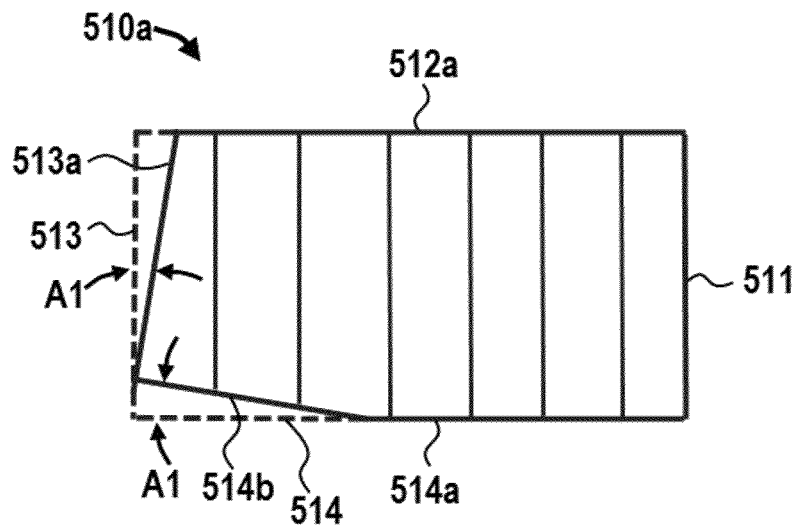
Figure 10B:
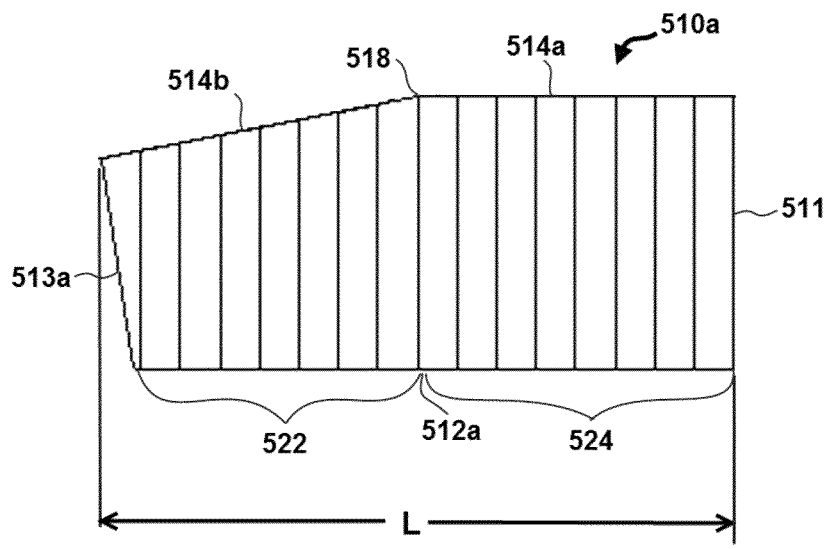
Figure 10C:
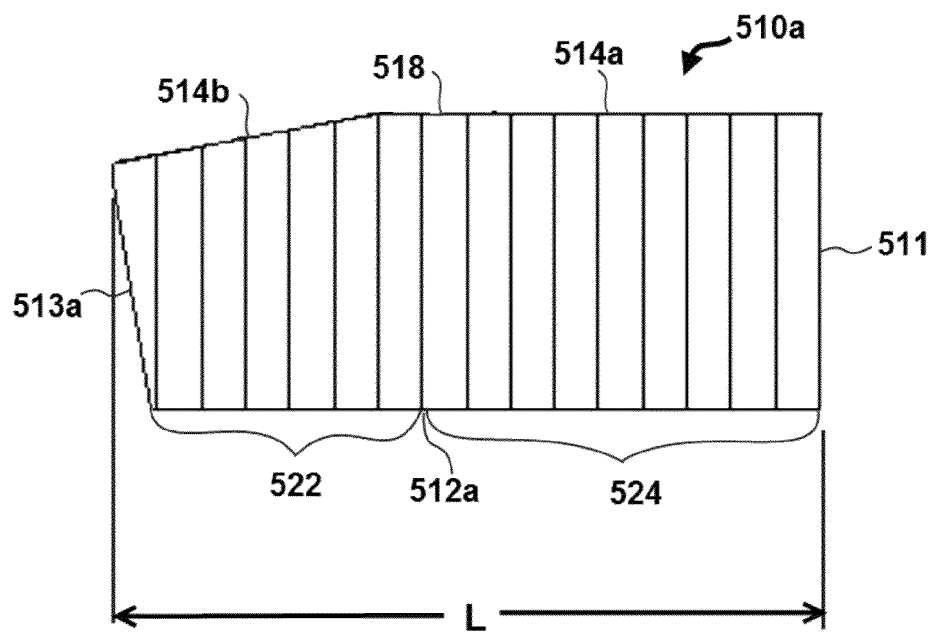
Figure 11:
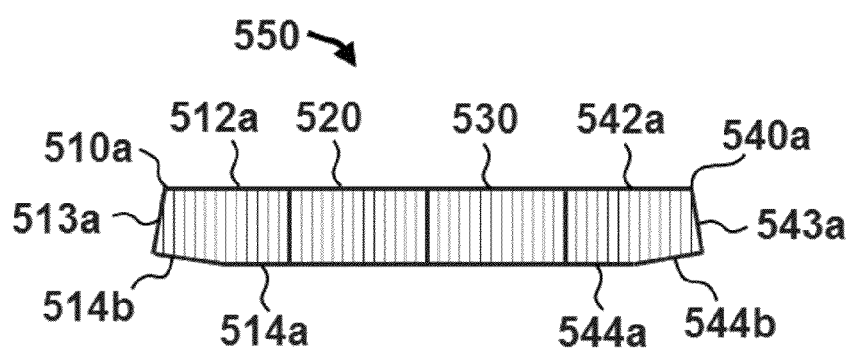

Referring now to FIGS. 9-11, a plurality of rectangular cross-section scintillation crystal blocks 510, 520, 530 and 540 are used to form an array 550 of blocks, as described in further detail below. In this exemplary embodiment, blocks 510 and 540 will be modified to have an asymmetric pentagonal cross-section, while blocks 520 and 530 will maintain their rectangular cross-section. Referring specifically now to FIG. 9, block 510 comprises a first side 511, a second side 512, a third side 513 and a fourth side 514. Similarly, block 540 comprises a first side 541, a second side 542, a third side 543 and a fourth side 544. In this embodiment, blocks 510 and 540 can be modified by tapering sides 513 and 514 and sides 543 and 544, respectively. In a specific embodiment, sides 513, 514 and 543, 544 can be tapered by grinding the sides. For purposes of clarity, the modification of block 510 will be described in detail below. It is understood that in this embodiment, the modification of block 540 is equivalent to that of block 510.

In the embodiment shown in FIG. 10A, side 513 has been tapered (e.g., ground) so that it forms side 513a that is no longer parallel with side 511. In addition, side 514 has been tapered (e.g., ground) so that it forms sides 514a and 514b. In this particular embodiment, the portion of side 514 that is proximal to side 513 has also been tapered to form side 514b, which is no longer parallel with sides 514a or 512. The resulting asymmetric pentagonal shape has side 514b that is angled with respect to side 514a (which is the original portion of side 514 that was proximal to side 511. The asymmetric pentagonal shape also has a second side 512a that is shorter than original second side 512. As shown and described herein, side 511 is the only side that maintains its original length and orientation in the modification of cross-section scintillation crystal block 510 into asymmetric pentagonal cross-section crystal block 510a. This modification, however, can be achieved with only two process steps, e.g. tapering of the original sides 513 and 514.

Referring now to FIGS. 10B and 10C, different configurations of asymmetric pentagonal cross-section crystal block 510a are shown. In FIG. 10B, while the overall configuration of block 510a is asymmetric, side 514b begins to taper or angle at intersection point 518 that is located at the midpoint of block 510a (e.g. side 514b extends across a plurality of eight crystals 522 and side 514a extends across a plurality of eight crystals 524 of block 510a). Side 514b is therefore longer than side 514a because side 514b extends across crystals 522 at an oblique angle, while side 514a extends perpendicularly across crystals 524. In this embodiment, side 512a is parallel to side 514a and side 512a extends across the length L of block 510a while side 514a extends to half of length L at intersection point 518 which is located at the midpoint of block 510a.

In contrast, the embodiments of FIG. 10C is configured so that side 514b extends across six crystals 522 and side 514a extends across ten crystals 524. In this configuration side 514b is shorter than side 514a, even though side 514b extends across crystals 522 at an oblique angle. In the embodiment of FIG. 10C, side 512a is parallel to side 514a and side 512a extends across the length L of block 510a while side 514a extends more than half of length L to intersection point 518.

In particular embodiments, the configuration shown in FIG. 10C may provide certain advantages over other configurations. For example, the cost of development and production may be decreased for the configuration shown in FIG. 10C due to factors such as the reduction in the amount of material is removed from block 510a (as compared to the material removed in the configuration of FIG. 10B). In the embodiment shown, for example, the amount of time for manufacturing (e.g. grinding or machining) can be reduced by as much as 44 percent.

The configuration of FIG. 10C can also increase detection sensitivity and simplify the decoding reflecting-film design. During operation, asymmetric cross-section scintillation crystal blocks provide optimal performance by utilizing a different reflecting film structure than that used with symmetric scintillation crystal blocks. However, the asymmetric reflecting film structure can increase the chance of error during mass production.

Therefore, it can be desirable to utilize an asymmetric block using symmetric reflecting film structure to reduce production errors and cost. The configuration of FIG. 10C is more compatible with the reflecting film structure of the symmetric detector blocks than the configuration of FIG. 10B. With blocks 510 and 540 modified to produce asymmetric pentagonal cross-section blocks 510a and 540a, an array 550 of blocks 510a, 520, 530 and 540a can be formed as shown in FIG. 11. In this embodiment, sides 513a and 543a are located at the ends of array 550 and are angled with respect to sides 512a and 542a, respectively. In addition, sides 514b and 544b are angled with respect to 514a and 544a. In exemplary embodiments, a plurality of block arrays equivalent to array 550 can be produced and coupled together such that sides 513a and 543a are adjacent. In particular embodiments, photomultiplier tubes (PMTs) can be coupled to arrays in a manner such that each PMT is coupled to multiple blocks. In specific embodiments, PMTs can be coupled to scintillation block arrays in a manner that provides photomultiplier quadrant sharing (PQS) as described in U.S. Pat. Nos. 5,319,204; 5,453,623; 6,956,214 and 7,238,943. In exemplary embodiments of the present disclosure, however, a PMT is coupled to surfaces 514b and 544b, which are angled with respect to surfaces 514a and 544a, respectively. As shown and described further below, exemplary embodiments comprise a PMT coupled to both rectangular scintillation blocks and asymmetric pentagonal scintillation blocks of array 550.

Figure 12:
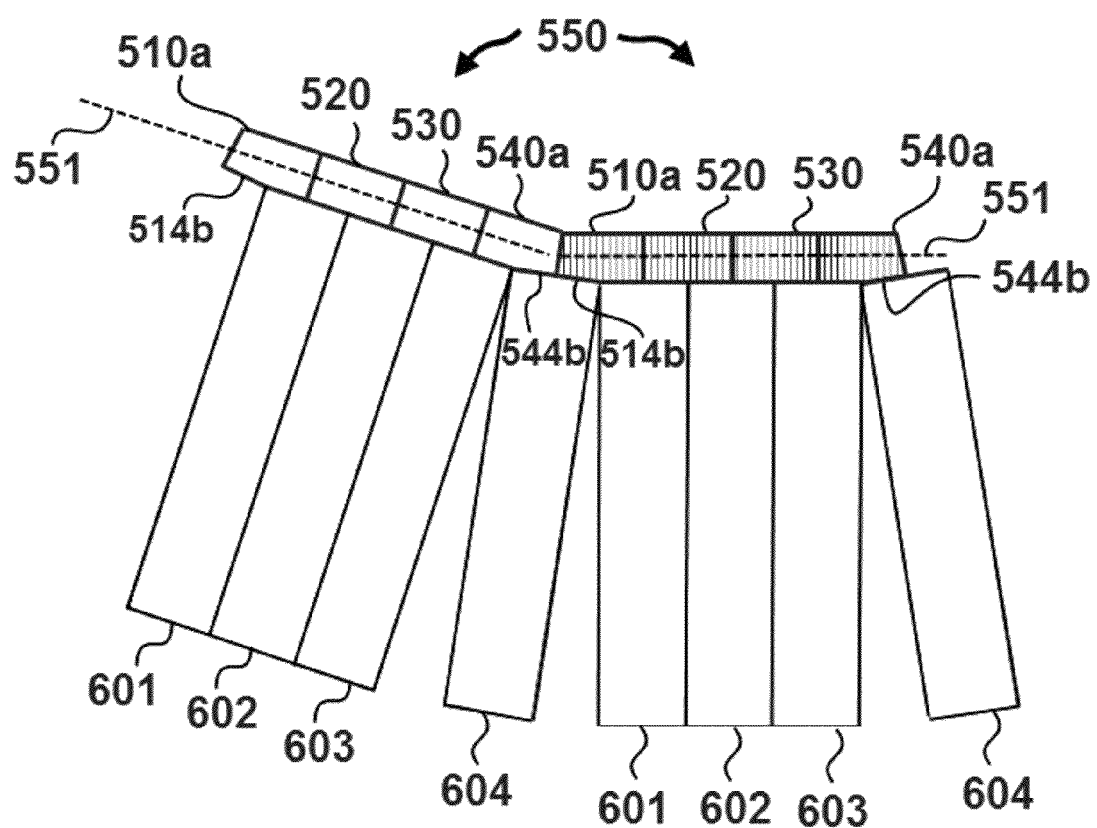
FIG. 12 displays the coupling of block arrays with PMTs.
Figure 13:
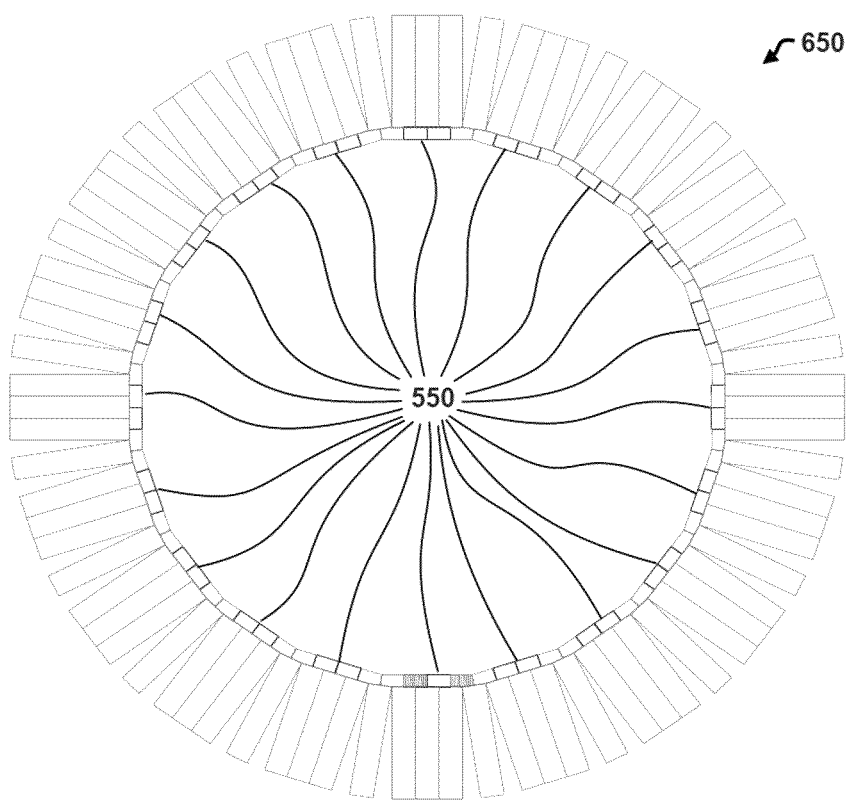
FIG. 13 displays arrays coupled together to form a 20-sided polygon detector ring.

As shown in FIG. 12, the coupling of block arrays 550 with PMTs results in three PMTs 601, 602, and 603 that are parallel to each other and perpendicular to a primary axis 551 of array 550 (e.g. an axis parallel to sides 512a and 514 shown in FIG. 10A). PMT 604, which is coupled to angled surfaces 514b and 544b, is angled (e.g., not parallel) with respect to PMTs 601, 602 and 603. The orientation of surfaces 513a, 514b, 543a and 544b allow a plurality of arrays 550 to be coupled together to form a ring, as shown in FIG. 13. This configuration can allow for the production of an effective, lower cost positron emission tomography (PET) scanner.

As shown in FIG. 13, a total of twenty arrays 550 can be coupled together to form a 20-sided polygon detector ring 650. The number of arrays 550 (e.g., the number of sides of the polygonal ring) can be used to determine the angle at which sides 513a, 514b, 543a and 544b are tapered. For example, the taper angle A1 (shown in FIG. 10A) can be calculated by the formula: A1=180°/N, where N is the number of arrays (e.g., sides) used to form the polygonal ring. Taper angle A1 is the angle between sides 514b and 514a (e.g., the acute angle between side 514b and a line parallel to side 514a). Taper angle A1 also describes the acute angle between side 513a and a line perpendicular to side 512a.

Figure 14:
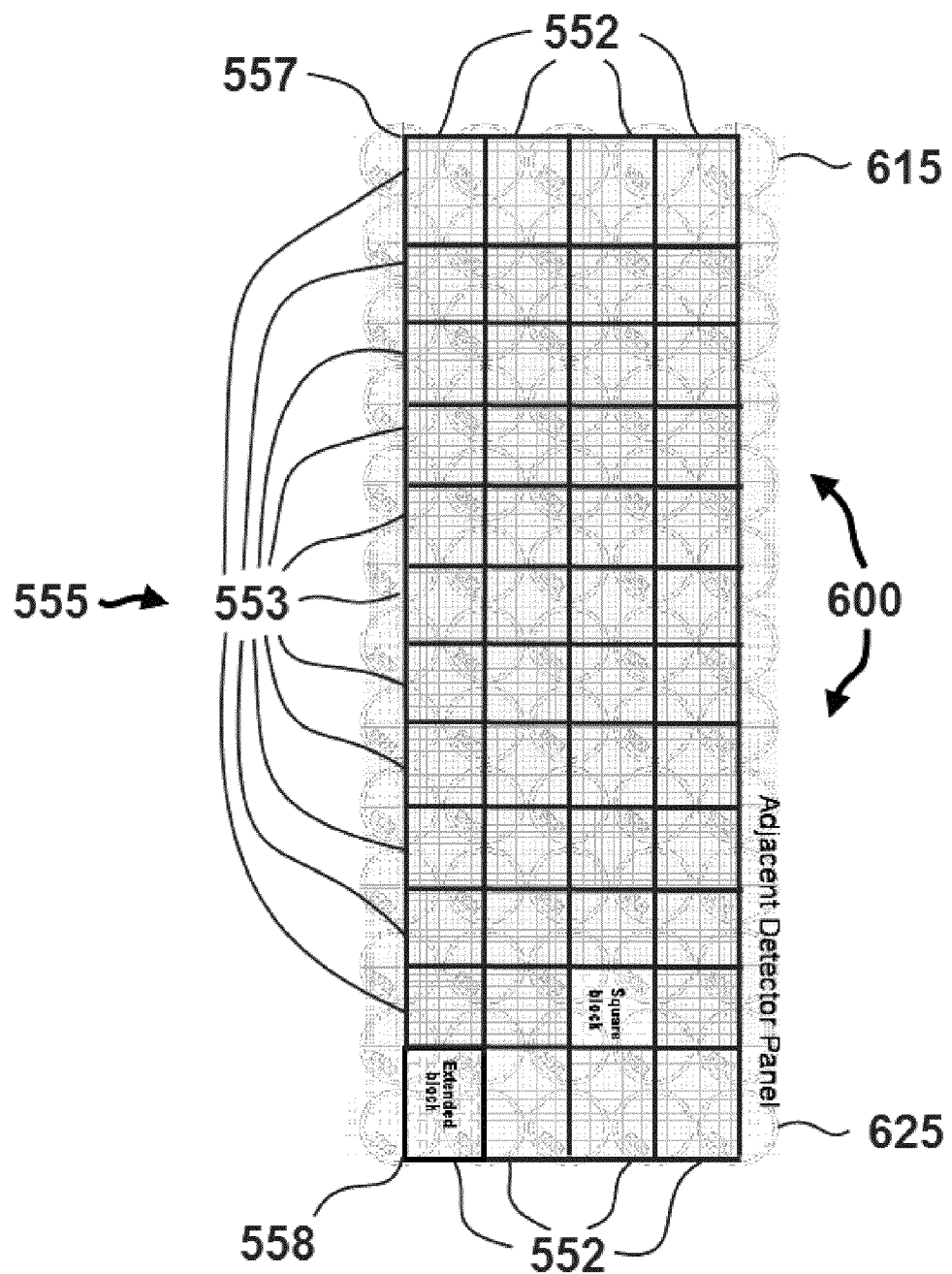
FIG. 14 displays a detector panel that comprises a plurality of blocks coupled to PMTs.

In certain embodiments, a detector ring may comprise scintillation arrays at each axial end that have crystal blocks with a greater axial length than circumferential length (where the axial end is viewed when looking from the center of the detector ring outward). For example, as shown in FIG. 14, an detector panel 555 comprises a plurality of blocks 552 and 553 coupled to PMTs 600. In this embodiment, blocks 553 are square. (e.g., when viewed from the center of detector ring 650 looking outwards toward arrays). In addition, each axial end 557, 558 of detector panel 555 has elongated blocks 552 that are rectangular when viewed from the same perspective.

It is understood that detector panel 555 can be formed from a plurality of arrays 550 and that blocks 552 and 553 can be placed in the positions of blocks 510a, 520, 530, and 540a shown in FIG. 12. The additional reference numbers provided in FIG. 14 are intended to indicate spatial positions of individual components when viewed outwardly from the center of a detector ring.

Elongated blocks 552 extend to cover more than half of PMTs 600 that are proximal to ends 557 and 558 of array (e.g., PMTs located on rows 615 and 625 as shown in FIG. 14. If square blocks were used on rows 615 and 625, one half of the PMTs on those rows would extend beyond the blocks. The use of rectangular elongated blocks 552 can increase the usable axial field of view of a detector ring incorporating such a configuration.

Without the elongated asymmetric PQS-block design, half a row of PMT would be wasted proximal to ends 557, 558 of detector panel 555. In a specific embodiment, 13×13 symmetric detector blocks (crystal size of 1.40×1.40×11 mm$^3$), made with the regular PQS detector design, are located inside the detector panel and edged by asymmetric blocks on both sides that form the outermost block rings proximal to ends 557, 558. In this specific embodiment, there are 40 regular (e.g. rectangular) PQS blocks and 8 asymmetric PQS blocks in each panel, and the detector arrays along the edge of the detector module are asymmetric arrays with 13×15 crystal pixels (crystal size of 1.40×1.66×11 mm3). A set of asymmetrically placed mirror film masks can be used to distribute the scintillation light for the asymmetric edge detector arrays.

In one specific embodiment, the detector blocks can be prepared in the following manner. The quadrant-sharing blocks (e.g. square block 553 and rectangular blocks 552) are first assembled (fixed by friction, pressure, or glued) into large detector panel 555. Next, the two outer rows of blocks of detector panel 555 can be slightly ground to taper on two sides. Specifically, on the PMT-coupling surface (e.g. surfaces 514a and 514b as well as 544a and 544b), the tapering starts at or proximal to the middle of the outermost row of blocks. As previously explained, the taper angle A1 is given by: A1=180°/N where N is the number of sides of the polygonal detector ring.

The detector side surface that is to be mated to an adjacent detector panel (e.g., 513a and 543a as shown in FIG. 11) can then be ground with an equivalent taper angle of 180°/N.

Alternatively, the steps described above can be achieved differently to produce the same result. For example, if the whole detector panel is P number of blocks wide (e.g., 4 blocks wide shown in FIG. 14). The panel can be first made into a strip that is P–2 blocks wide (e.g. 2 blocks total in the embodiment shown) for the central un-tapered region. The two tapered crystal block strips along the two outer edges in can be ground either (i) with each block individually ground into the desired shape and then glued onto the untapered central-region section, or (ii) the blocks on edge rows can be glued together into a one-block wide strip first and then this long one-block strip are ground into the desired shape. Then the ground strip of blocks can be glued onto the central-region untapered blocks.

Figure 1:
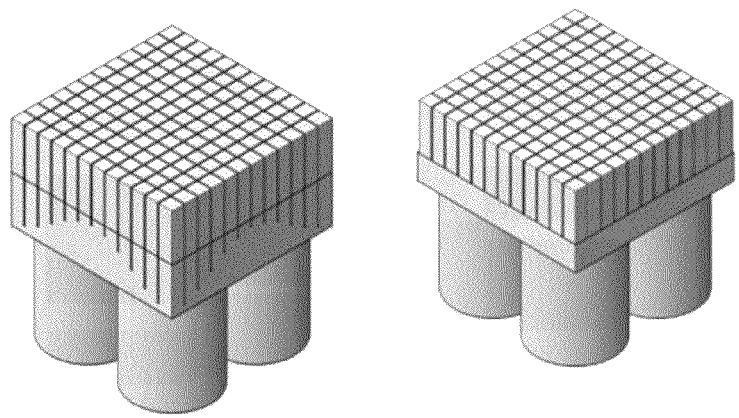
FIG. 1 displays a conventional PET detector array using external light guides to distribute light from scintillation detector pixels to four PMT.
Figure 2:
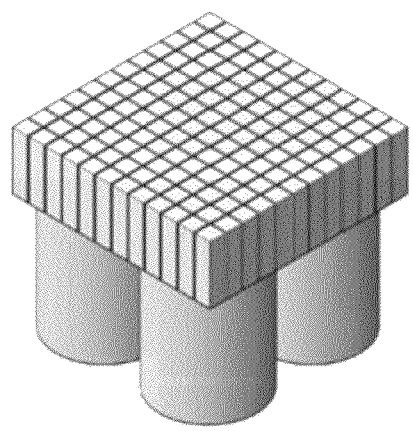
FIG. 2 displays a conventional PET array using internal light distribution to distribute light to four PMT.
Figure 3:
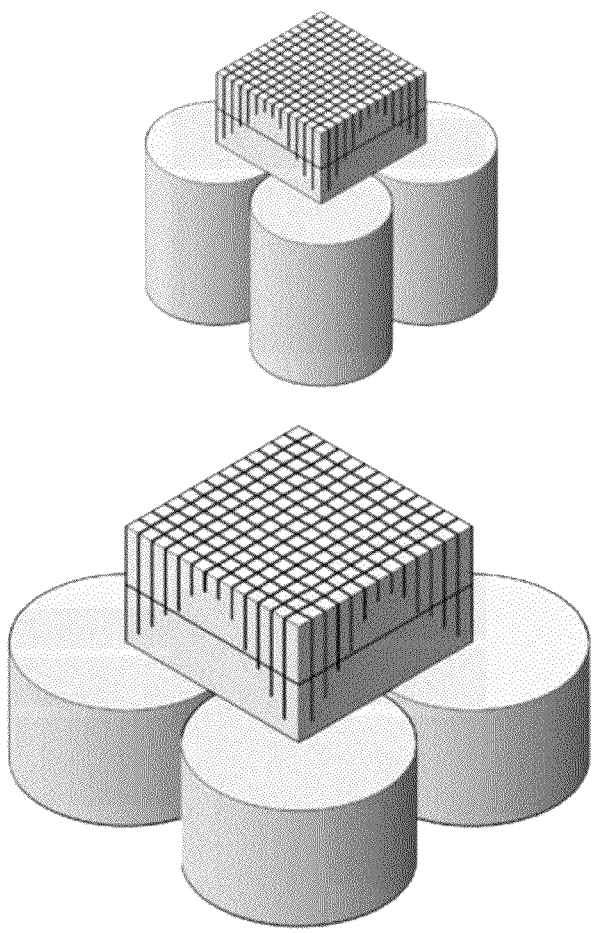
FIG. 3 displays illustrates a PQS array using an external light guide and the same size PMT as used in the embodiments of FIGS. 1 and 2.
Figure 4:
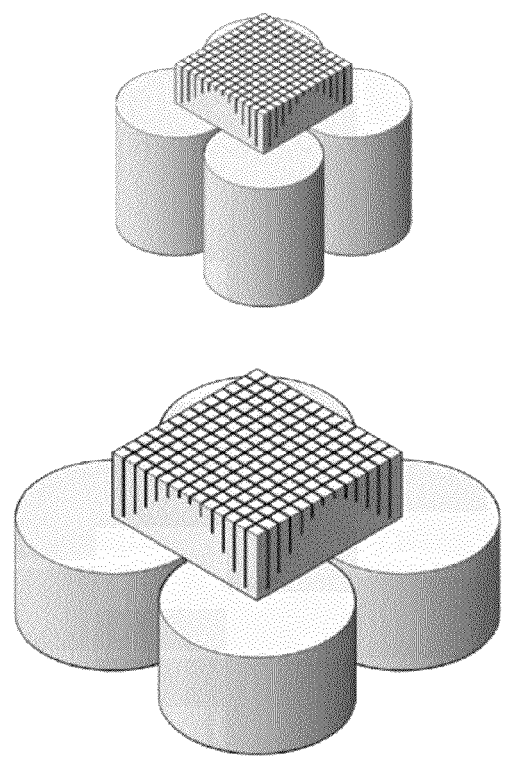
FIG. 4 displays a PQS array using internal light distribution to increase resolution or reduce PMT cost.
Figure 5:
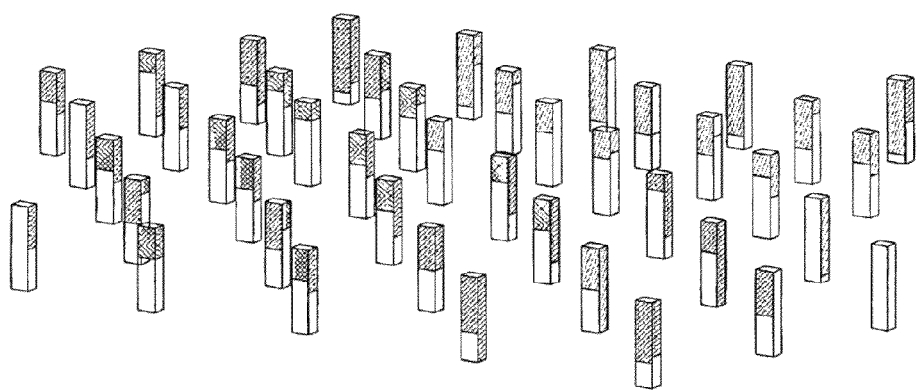
FIG. 5 displays partial reflectors applied to the detector pixels in a block.
Figure 6:
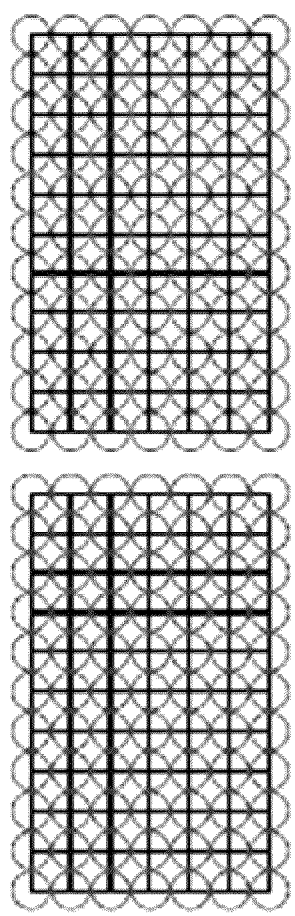
FIG. 6 displays PQS detector design implemented in the form of rectangular detector panels.
Figure 7:
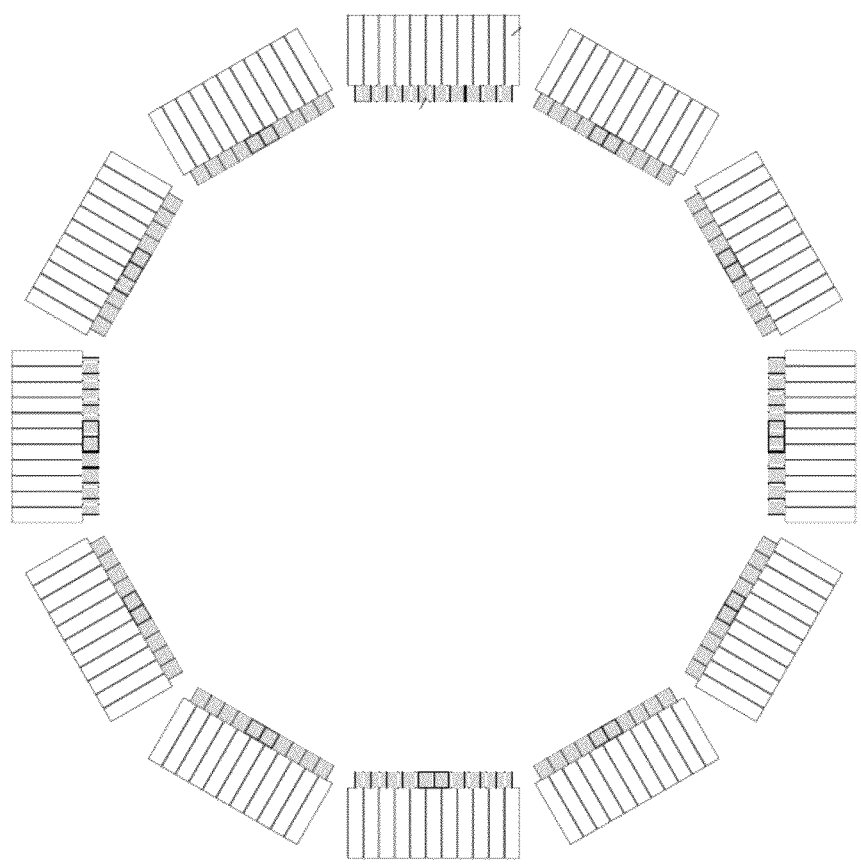
FIG. 7 displays PET detectors forming a detection ring.

With the detector panels 555 formed, they can then be butted (fitted) together along the tapered side (e.g. sides 513a and 543a) to form a polygonal detector ring 650 as shown in FIG. 13 with no detection gaps. As shown in FIGS. 12 and 13, the detector panel is coupled directly to the PMT's. The PMT's that are completely inside a detector panel are coupled in the normal PQS arrangement (e.g., as shown in FIGS. 3 and 4).

The row of PMT's that are riding over two adjacent detector panels (e.g. PMTs 604 in FIG. 12 are angled from the PMTs that are inside the detector panel (e.g. PMTs 601, 602, and 603) by the same taper angle A1, which is equal to of 180°/N, where N is the number of sides in the polygonal detector ring. PMTs 604 are also coupled to the tapered detector arrays/blocks of each panel, in the PQS arrangement (e.g., as shown in FIGS. 3 and 4).

Accordingly a solid detector ring without detection gap can be made using the PQS detector configuration as shown in FIG. 13. In the particular embodiment shown in FIG. 13, a 47.7 centimeter diameter detector ring can be formed by twenty arrays 550 with no detector gap between two panels and no waste PMT usage, allowing the PMT economy to be maximized. If each array 550 is arranged according to the configuration of detector panel 555 shown in FIG. 14, the detector will utilize 1,040 regular circular PMTs to decode 166,400 crystals.

If two cameras with different detector ring-diameters have the same number of sides of the polygonal detector ring, the taper angles for both cameras are the same. However, the camera with the larger diameter has wider detector panels with more regular (untapered) rectangular blocks.

Embodiments that utilize an arc or partial polygonal ring (rather than a complete polygonal ring) with N panels can be treated as a partial detector ring of M degrees, then the taper angles will be M/(2N).

In summary, advantages of disclosed embodiments include (but are not limited to): (1) a higher crystal/PMT decoding ratio or a higher detection resolution allowing the PMT economy to be maximized with PQS design using LYSO detectors; (2) no gap between two asymmetric pentagonal shaped detector panels, eliminating the system-rotation requirement and maximizing sensitivity; and (3) no software filling of detector-gaps on the detected data, which increases noise and decreases image resolution. In addition, for a "Time-of-Flight" (TOF) PET detector, the software gap filling is not possible for the lack of TOF information on the missing line-of response in the detector gaps.

Figure 8:
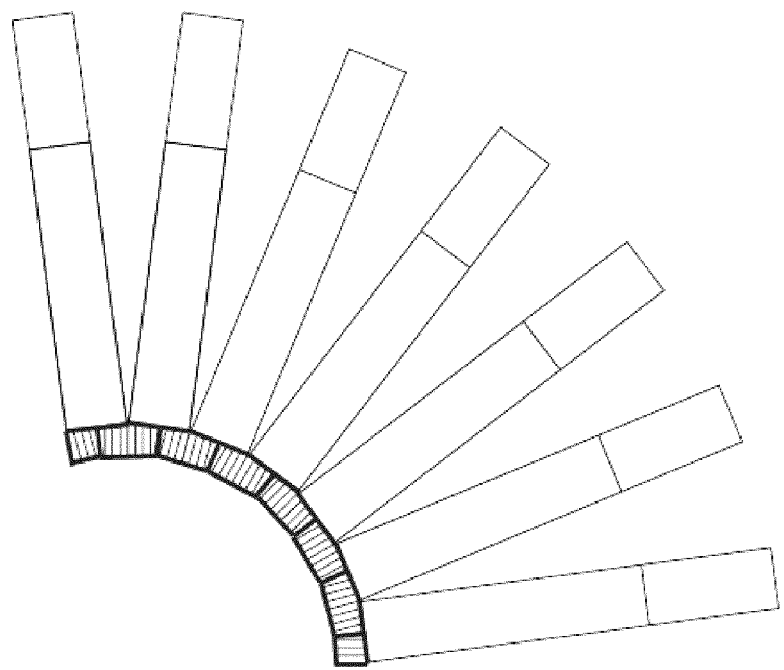
FIG. 8 displays four surfaces of each detector block precisely tapered to form a symmetric pentagon.

Additional advantages include reduced labor and manufacturing requirements. In one embodiment, instead of grinding 960 individual pentagonal blocks (as done in animal-scale PET detectors utilizing all tapered pentagonal blocks as shown in FIG. 8), only 20 grinds of pentagonal panels are required. This can reduce by a factor of 48 the labor of block grinding, which requires high precision, and further reducing the PET detector production cost. The mechanical design for gantry and detector panel support, as well as detector-cooling design, can also be simplified using the configurations disclosed herein. Furthermore, convenience for system maintenance and decreased production steps reduces the risk of detector breakage. In full solid ring systems with all pentagon blocks glued together, if one part of the detector is broken the whole expensive ring may become useless.

Accordingly, exemplary apparatus and method described herein provide numerous benefits and advantages over existing technologies. As illustrated and described above, prior art systems and methods typically required four modification steps in order to produce symmetric pentagonal cross-section crystal blocks. Each modification step increased the likelihood of damaging the crystal block due to the shearing forces exerted. In exemplary embodiments, each crystal block can comprise a plurality of small detector pixels glued together with a reflecting film (e.g., a weak polymer film or white paint) between each pixel. In certain embodiments, the high shearing force of grinding can separate the film from the glue, or the glue from the crystal pixels, thus damaging the crystal block and rendering it useless for its intended purpose.

Reducing the manufacturing steps by fifty percent (from four to two) to produce the asymmetric pentagonal cross-section crystal block can increase production yield due to fewer blocks being damaged as compared to prior techniques.

In one specific example, a block that is 4 cm×4 cm×2 cm can cost $1,300 in raw material alone. If a block is damaged, both the labor and material (e.g. reflecting film) costs required for building the block are also lost. Assuming approximately $200 in labor cost, each broken block can cost $1,500.

In one exemplary apparatus, a PET scanner utilizing 1,000 blocks, a five percent breakage rate can increase cost $75,000 (1,000 blocks×0.05 breakage rate×$1,500/block) per apparatus. In order to produce a 1,000 block PET scanner, prior art techniques would require four surfaces to be ground on each block, or 4,000 surfaces total. In exemplary embodiments disclosed herein, only 500 blocks would require modification, assuming there were two rectangular blocks between two asymmetric pentagonal blocks in each array. In addition, only two sides on each pentagonal block would require tapering (e.g., grinding). Accordingly, only 1,000 surfaces would need to be modified, a reduction of 75 percent as compared to the prior art techniques. With equivalent breakage risks in each manufacturing step used in prior art and current embodiments, the breakage rate for the total number of blocks would accordingly also be reduced by 75 percent in the current embodiments.

Assuming a five percent breakage rate of blocks used in the prior art techniques, a 75 percent reduction results in a 1.25 percent breakage rate for embodiments utilizing the manufacturing methods disclosed herein. For an entire apparatus utilizing 1,000 blocks, the reduction in breakage of individual blocks would reduce the breakage costs from $75,000 to $18,750 for a net reduction in manufacturing costs of $56,250.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
1. S. Surd, A. Kuhn, M. E. Werner, A. E. Perkins, J. Kolthammer, and J. S. Karp, Performance of Philips Gemini TF PET/CT Scanner with Special Consideration for Its Time-of-Flight Imaging Capabilities, J Nucl Med. Vol. 48, no. 3, pp: 471-480, 2007.
2. Xie, S, Ramirez, R, Liu, Y, Uribe, J, Li, H, Wang, Y, Xing, T, Baghaei, H, Wong, W-H. A Pentagon Photomultiplier-Quadrant-Sharing BGO Detector for a Rodent Research PET (RRPET). IEEE Transactions on Nuclear Science 52:210-216, 2/2005
3. Wong W H, Li H, Xie S, Ramirez R, Kim S, Uribe J, Baghaei H: Design of an Inexpensive High-Sensitivity Rodent-Research PET Camera (RRPET). 2003 Nuclear Science, IEEE Transactions, Volume: 50 Issue: 5, October 2003, Page(s): 1357-1363.
4. W-H. Wong, H. Li, H. Baghaei, Y. Wang, S. Xie, R. Ramirez, Y. Zhang, S. Kim, J. Liu, S. Liu, B. Patt. Preliminary Results of a Low Cost and High Sensitivity Rodent- Research PET (RRPET) and PET/CT (X-PET), 2005 IEEE Nuclear Science Symposium and Medical Imaging Conference, Oct. 23-29, 2005.

5. Rocio A. Ramirez, Shitao Liu, Jiguo Liu, Yuxuan Zhang, Soonseok Kim, Hossain Baghaei, Hongdi Li, Yu Wang and Wai-Hoi Wong: High-Resolution L(Y)SO Detectors Using PMT-Quadrant-Sharing for Human & Animal PET Cameras, IEEE Transactions on Nuclear Science, 55(3):862-869. 2008.

6. Yuxuan Zhang, R. Ramirez, H. Li, S. Liu, S. An, C. Wang, H. Baghaei, W.-H. Wong. The System Design, Engineering Architecture and Preliminary Results of a Lower-cost High-Sensitivity High-Resolution Positron Emission Mammography Camera. Accepted for publication in the IEEE Transactions on Nuclear Science.

7. Rocio A. Ramirez, Yuxuan Zhang, Shitao Liu, Hongdi Li, Hossain Baghaei, Shaohui An, Chao Wang, Meei-Ling Jan and Wai-Hoi Wong. "A Lower-Cost High-Resolution LYSO Detector Development for Positron Emission Mammography (PEM)". Accepted for publication in the IEEE Transactions on Nuclear Science, 2009.

8. Ramirez, R, Shitao Liu, Hossain Baghaei, Yuxuan Zhang, Hongdi Li, Shaohui An, Chao Wang and Wai-Hoi Wong. "Performance Characteristics of High-resolution 16×16 L(Y)SO Detector Blocks for Whole-body PET". Submitted for publication in the IEEE Transactions on Nuclear Science. 2009.

9. Wong, W-H, Yokoyama, S, Uribe, J, Baghaei, H, Li, H, Wang, J, Zhang, N. An elongated position sensitive block detector design using the PMT quadrant-sharing configuration and asymmetric light partition. IEEE Transactions on Nuclear Science 46(3):542-545, 6/1999.

10. Asymmetrically Placed Cross-Coupled Scintillation Crystals, U.S. Pat. No. 7,238,943, Awarded Jul. 3, 2007.

The invention claimed is:

1. An apparatus comprising:
a plurality of photosensors; and
a first array of scintillation crystals coupled to the plurality of photosensors;
wherein the first array of scintillation crystals comprises a first rectangular cross-section crystal block positioned between a first pentagonal cross-section crystal block and a second pentagonal cross-section crystal block, wherein:
the first pentagonal cross-section crystal block comprises a first side adjacent to the first rectangular cross-section block, the first side of the first pentagonal cross-section crystal block being perpendicular to a second side and to a third side of the first pentagonal cross-section crystal block; and
the second pentagonal cross-section crystal block comprises a first side adjacent to the second rectangular cross-section block, the first side of the second pentagonal cross-section crystal block being perpendicular to a second side and to a third side of the second pentagonal cross-section crystal block.

2. The apparatus of claim 1 further comprising a second rectangular cross-section crystal block positioned between the first pentagonal cross-section crystal block and the second pentagonal cross-section crystal block.

3. The apparatus of claim 2 further comprising N number of arrays of scintillation crystals coupled to the plurality of photosensors configured as a continuous polygonal detector-ring.

4. The apparatus of claim 1 wherein:
the first pentagonal cross-section crystal block comprises a fourth side configured at a first taper angle relative to the first and third sides of the first pentagonal cross-section crystal block;
the first pentagonal cross-section crystal block comprises a fifth side configured at a second taper angle relative to the second side of the first pentagonal cross-section crystal block; and
the first taper angle is equal to the second taper angle.

5. The apparatus of claim 4 wherein the first and second taper angles are equal to (180°/N).

6. The apparatus of claim 1 wherein the photosensors are photomultiplier tubes and wherein:
a first photomultiplier tube and a second photomultiplier tube are adjacent and parallel to each other;
the first photomultiplier tube and the second photomultiplier tube are disposed between a third photomultiplier tube and a fourth photomultiplier tube;
the third photomultiplier tube and the fourth photomultiplier tube are not parallel to each other; and
the third photomultiplier tube and the fourth photomultiplier tube are not parallel to the first and second photomultiplier tubes.

7. The apparatus of claim 1 wherein the apparatus is configured as a positron emission tomography detector and wherein:
the first pentagonal cross-section crystal block comprises a first side that is parallel to a second side;
the first side extends across the length of the first pentagonal cross-section crystal block; and
the second side extends more than half of the length of the first pentagonal cross-section crystal block.

8. An apparatus comprising:
a plurality of photomultiplier tubes coupled to a plurality of scintillation crystal arrays configured as a continuous detector-ring, wherein:
each scintillation crystal array comprises a plurality of rectangular cross-section crystal blocks and a plurality of asymmetric pentagonal cross-section crystal blocks;
each of the rectangular cross-section crystal blocks are positioned between a pair of asymmetric pentagonal cross-section crystal blocks; and
the plurality of asymmetric pentagonal cross-section crystal blocks comprises a first asymmetric pentagonal cross-section crystal block comprising:
a first side that is parallel to a second side;
the first side extends across the length of the first pentagonal cross-section crystal block; and
the second side extends more than half of the length of the first pentagonal cross-section crystal block.

9. The apparatus of claim 8 wherein each of the rectangular cross-section crystal blocks are adjacent to an asymmetric pentagonal cross-section crystal block and to a rectangular cross-section crystal block.

10. The apparatus of claim 8 wherein a pair of rectangular cross-section crystal blocks are positioned between a pair of asymmetric pentagonal cross-section crystal blocks.

11. The apparatus of claim 8 wherein the continuous detector-ring comprises a first and second axial end, the first and second axial end comprising a plurality of scintillation crystal arrays having crystal blocks with a greater axial length than circumferential length.

12. An array of scintillation crystal blocks, comprising:
a first asymmetric pentagonal cross-section scintillation crystal block;

a second asymmetric pentagonal cross-section scintillation crystal block;

a rectangular cross-section scintillation crystal block disposed between the first and second asymmetric pentagonal cross-section scintillation crystal blocks, wherein the first and second asymmetric pentagonal cross-section scintillation crystal blocks each comprise a first side that is perpendicular to a second side and perpendicular to a third side.

13. The array of scintillation crystal blocks of claim 12 wherein the rectangular cross-section scintillation crystal block is adjacent to the first side of the first and second asymmetric pentagonal cross-section scintillation crystal blocks.

* * * * *